United States Patent
Miyahara et al.

(10) Patent No.: US 8,345,246 B2
(45) Date of Patent: Jan. 1, 2013

(54) RUNNING YARN LINE INSPECTION METHOD AND CARBON FIBER MANUFACTURING METHOD USING THEREOF

(75) Inventors: Kazuhisa Miyahara, Otsu (JP); Kouji Kagitani, Otsu (JP); Hiroki Nakajima, Otsu (JP)

(73) Assignee: Toray Industries, Inc., Tokyo (JP)

( * ) Notice: Subject to any disclaimer, the term of this patent is extended or adjusted under 35 U.S.C. 154(b) by 493 days.

(21) Appl. No.: 12/599,443

(22) PCT Filed: Apr. 25, 2008

(86) PCT No.: PCT/JP2008/058070
§ 371 (c)(1),
(2), (4) Date: Nov. 9, 2009

(87) PCT Pub. No.: WO2008/139892
PCT Pub. Date: Nov. 20, 2008

(65) Prior Publication Data
US 2010/0157301 A1    Jun. 24, 2010

(30) Foreign Application Priority Data
May 11, 2007    (JP) .................................. 2007-126370

(51) Int. Cl.
*G01N 21/84*    (2006.01)
*G01N 21/86*    (2006.01)
(52) U.S. Cl. .... 356/431; 356/429; 356/430; 250/559.11
(58) Field of Classification Search ........................ None
See application file for complete search history.

(56) References Cited

U.S. PATENT DOCUMENTS

| | | | | |
|---|---|---|---|---|
| 3,765,777 A | * | 10/1973 | Williams, Jr. | 356/430 |
| 4,103,177 A | * | 7/1978 | Sanford et al. | 250/559.03 |
| 4,675,730 A | * | 6/1987 | Adomaitis et al. | 348/131 |
| 5,313,692 A | * | 5/1994 | Mizuuchi et al. | 28/187 |
| 5,319,578 A | * | 6/1994 | Lawson et al. | 250/559.24 |
| 5,383,017 A | * | 1/1995 | Schurch | 356/238.3 |
| 5,420,439 A | * | 5/1995 | Landwehrkamp et al. | 250/559.46 |
| 5,684,598 A | * | 11/1997 | Harke et al. | 356/430 |
| 6,760,102 B2 | * | 7/2004 | Harmstorf | 356/238.1 |
| 2001/0022656 A1 | * | 9/2001 | Henze et al. | 356/238.3 |
| 2010/0032049 A1 | * | 2/2010 | Wadahara et al. | 139/435.1 |

FOREIGN PATENT DOCUMENTS

DE    3832984 A1    4/1990
(Continued)

OTHER PUBLICATIONS

International Search Report dated May 27, 2008, application No. PCT/JP2008/058070.
Supplementary European Search Report dated May 3, 2012, application No. EP08740872.

*Primary Examiner* — Gordon Stock, Jr.
(74) *Attorney, Agent, or Firm* — RatnerPrestia

(57) ABSTRACT

A running yarn line inspection method inspects yarn lines running in parallel in the same surface. The running yarn line inspection method is provided with a first illumination means and a line sensor for imaging the yarn lines on the side of the first surface of the running surface of the yarn lines and a second illumination means on the side of the second surface, and comprises a data processing means which processes data obtained by the line sensor and a recording means which records data processed by the data processing means with time.

9 Claims, 10 Drawing Sheets

FOREIGN PATENT DOCUMENTS

| | | |
|---|---|---|
| DE | 4320874 C1 | 2/1995 |
| JP | 61-114115 | 5/1986 |
| JP | 147825 A | 6/1993 |
| JP | 6-108346 A | 4/1994 |
| JP | 7-5119 A | 1/1995 |
| JP | 7-5120 A | 1/1995 |
| JP | 7-300280 A | 11/1995 |
| JP | 8-25691 B2 | 3/1996 |
| JP | 2623149 B2 | 6/1997 |
| JP | 2004-277938 | 10/2004 |

* cited by examiner

RUNNING YARN LINE INSPECTION METHOD AND CARBON FIBER MANUFACTURING METHOD USING THEREOF

This application is a U.S. National Phase Application of PCT International Application No. PCT/JP2008/058070, filed Apr. 25, 2008, which claims priority to Japanese Patent Application No. 2007-126370, filed May 11, 2007, the content of these applications being incorporated by reference herein in their entirety.

FIELD OF THE INVENTION

The present invention relates to a running yarn inspection method for finding whether or not multiple yarns running in parallel to each other in a plane have defects and for finding the states of the defects, if any, by processing data obtained by an optical means. The defects of running yarns found by the running yarn inspection method of the invention include, for example, fluffs and fuzz formed on the running yarns and fluctuations in yarn width. The running yarn inspection method of the invention can be preferably used for inspecting defects of carbon fiber yarns in a carbon fiber production process.

BACKGROUND OF THE INVENTION

In a production process of a yarn comprising a bundle of numerous continuous filaments such as synthetic fibers, there is a case where fluffs or fuzz occur on the yarn owing to broken filaments and the like. Further, owing to broken filaments and the like, it can happen that filaments may come off from the yarn, to decrease the number of filaments constituting the yarn or to cause yarn splitting. Moreover, it can happen that all the filaments constituting the yarn may be broken to cut the yarn. Most of these defects (disorders) occurring on the yarn are caused by external or internal structural changes of the yarn based on variations of various process conditions such as the variations of tension and heat treatment temperature in the production process. Moreover, fluffs or fuzz once separated from the yarn and suspended in air may reattach to the yarn in the production process of the yarn.

These defects of yarns greatly affect the quality of yarns themselves and the quality of textile products formed of the yarns. Therefore, it is very important for quality control of yarns themselves and textile products, to accurately detect and identify the defects of yarns. In addition, if the states of the yarns running in a yarn production process can be constantly monitored to early identify the changes in the states of yarns or frequent occurrences of defects caused by the variations of process conditions, the yield in the yarn production process can be enhanced. That is, it is important to identify the defects of running yarns online.

Most of yarn production processes employ a method in which multiple yarns are made to run in parallel to each other for simultaneous production of multiple yarns. In such a production process, it is important for quality control of produced yarns themselves and of yarn package obtained by winding the produced yarns that the multiple yarns running in parallel to each other are simultaneously inspected and that the defects of every yarn are detected for obtaining the information on the defects of every yarn.

As a traditional method for constantly monitoring the state of a yarn for detecting the defects occurring on the yarn, proposed is a method in which an inspection region larger than the width of a yarn is irradiated with the light from a light projecting section, so that a light receiving section may detect the light intensity transmitted or reflected when the running yarn passes through the inspection region, for detecting the defects occurring on the yarn in reference to the changes of light intensity (see Patent Literature 1). However, the inspection method described in Patent Literature 1 requires at least one light receiving section for one yarn. For example, in a process for simultaneously producing 100 yarns, 100 light receiving sections are necessary. Therefore, this inspection method is very costly for inspecting all yarns.

As a method for inspecting the defects of multiple yarns simultaneously at low cost, proposed is a method in which a light projecting means is set up on one lateral side of the yarns while a light receiving means is set up on the other side beyond the yarns, with the yarns placed inside of, immediately above or immediately below the luminous flux, to detect each fuzz formed on a yarn when the fuzz intercepts the light (see Patent Literature 2). However, according to the inspection method described in Patent Literature 2, which of the yarns placed between the light projecting means and the light receiving means has been found to have a defect cannot be determined. Therefore, the information on the defects of every yarn cannot be obtained. Further, in the case where a flat defect thinly spreads over the surface of a yarn, since the quantity of intercepted light is small, it is difficult to detect such a defect by this inspection method.

As a method for inspecting the defects of yarns in a yarn sheet in which numerous yarns are laid out parallel to each other, proposed is a method in which the yarns are imaged using a camera to detect the defects of the yarns by image processing (see Patent Literature 3). However, according to the inspection method described in Patent Literature 3, the number of yarns that can be inspected simultaneously is small due to the difficulty of the resolution in the width direction of the camera. For example, it is difficult to simultaneously inspect about 100 yarns running in parallel to each other, and further in the case where the multiple yarns are inspected simultaneously, the yarns found to have defects cannot be identified, not allowing the information on the defects of every yarn to be obtained.

Patent Literature 1: JP 7-300280 A
Patent Literature 2: JP 61-114115 A
Patent Literature 3: JP 2004-277938 A

SUMMARY OF INVENTION

Exemplary embodiments of the invention provide a running yarn inspection method, in which in a condition where multiple yarns each of which comprises a bundle of numerous continuous filaments run in parallel to each other in a plane, not only whether or not the every yarn has defects but also the states of the defects, if any, can be identified by processing data obtained by an optical means.

Exemplary embodiments of the invention also provide a process for producing carbon fiber yarns each of which comprises a bundle of numerous continuous single carbon fibers using the running yarn inspection method of the invention.

The running yarn inspection method of the invention in an exemplary embodiment is a method for inspecting multiple yarns running in parallel to each other in a plane, comprising:

(a) a step of illuminating from both sides of a first face and a second face of a yarn running plane (e.g., by illuminating the yarn running plane from a first face side of the yarn running plane and a second face side of the yarn running plane) and receiving the light reflected from the every yarn and the light transmitted through the clearances formed between the respectively adjacent yarns simultaneously at a location in opposite to the first face by an imaging means, (b) a step of processing received light data obtained by the imaging means, by a data processing means, and (c) a step of recording a part or all of the data obtained by the data processing means, into a recording means with the lapse of time, wherein (d) the data processing by the data processing means comprises:

(d-1) a first data processing procedure for specifying positions of the yarns from the received light data and calculating yarn widths at the positions of the yarns and lightness values in the transverse direction of the yarns, and (d-2) a second data processing procedure for comparing the data obtained by the first data processing procedure with a predetermined threshold value, and/or a third data processing procedure to perform adding and averaging calculations for a predetermined number of scanned data sets obtained from consecutive measurements in the running direction of the yarns by the first data processing procedure, followed by calculating the differences between the sums and those between the averages of the data in the consecutive data sets.

In the running yarn inspection method of the invention, it is preferred that the imaging means is a line sensor.

In the running yarn inspection method of the invention, the data obtained from the second data processing procedure and/or the third data processing procedure may be used to specify defects of yarns and/or yarns having defects.

In the running yarn inspection method of the invention, the illumination from the second face side may also be obtained by reflecting the illumination from the first face side by a reflection plate installed on the second face side.

In the running yarn inspection method of the invention, it is preferred that the imaging means, the visual field of the imaging means on the running yarn plane and the illumination from the second face side are positioned on one straight line, and the imaging means is positioned at a location not receiving the regular reflection light of the illumination from the first face side on the running yarn plane.

In the running yarn inspection method of the invention, the difference data obtained by the third data processing procedure from the lightness values in the transverse direction of the yarns at the positions specified by the first data processing procedure may be compared with a threshold value predetermined by the second data processing procedure.

In the running yarn inspection method of the invention, only the data portions including yarns having defects may be extracted from the temporally continuous lightness data obtained by the first data processing procedure and stored as two-dimensional data by the recording means.

In the running yarn inspection method of the invention, whether or not the lightness difference data obtained by the data processing means is periodic may also be determined.

A carbon fiber production process in an embodiment of the invention comprises a carbonization treatment step of treating multiple precursor yarns each of which comprises a bundle of numerous continuous filaments running parallel to each other for carbonization, a carrying step of letting multiple carbon fiber yarns derived from the carbonization treatment step run in parallel to each other in a plane, and a winding step of winding the respective carbon fiber yarns having passed through the carrying step, wherein an inspection step of inspecting the multiple carbon fiber yarns using the running yarn inspection method of the abovementioned present invention is included in a place where the multiple carbon fiber yarns run in parallel to each other in the plane in the carrying step.

According to the running yarn inspection method in an embodiment of the invention, in a state that multiple yarns each of which comprises a bundle of numerous continuous filaments run in parallel to each other in a plane, not only whether or not the multiple yarns have defects respectively but also the states of the defects, if any, can be identified online by processing the data obtained by an optical means. Therefore, if the running yarn inspection method in an embodiment of the invention is used, the quality control of the every yarn produced by a yarn production process of simultaneously producing multiple yarns can be appropriately and promptly performed.

REFERENCE SIGNS LIST

Figure 1:
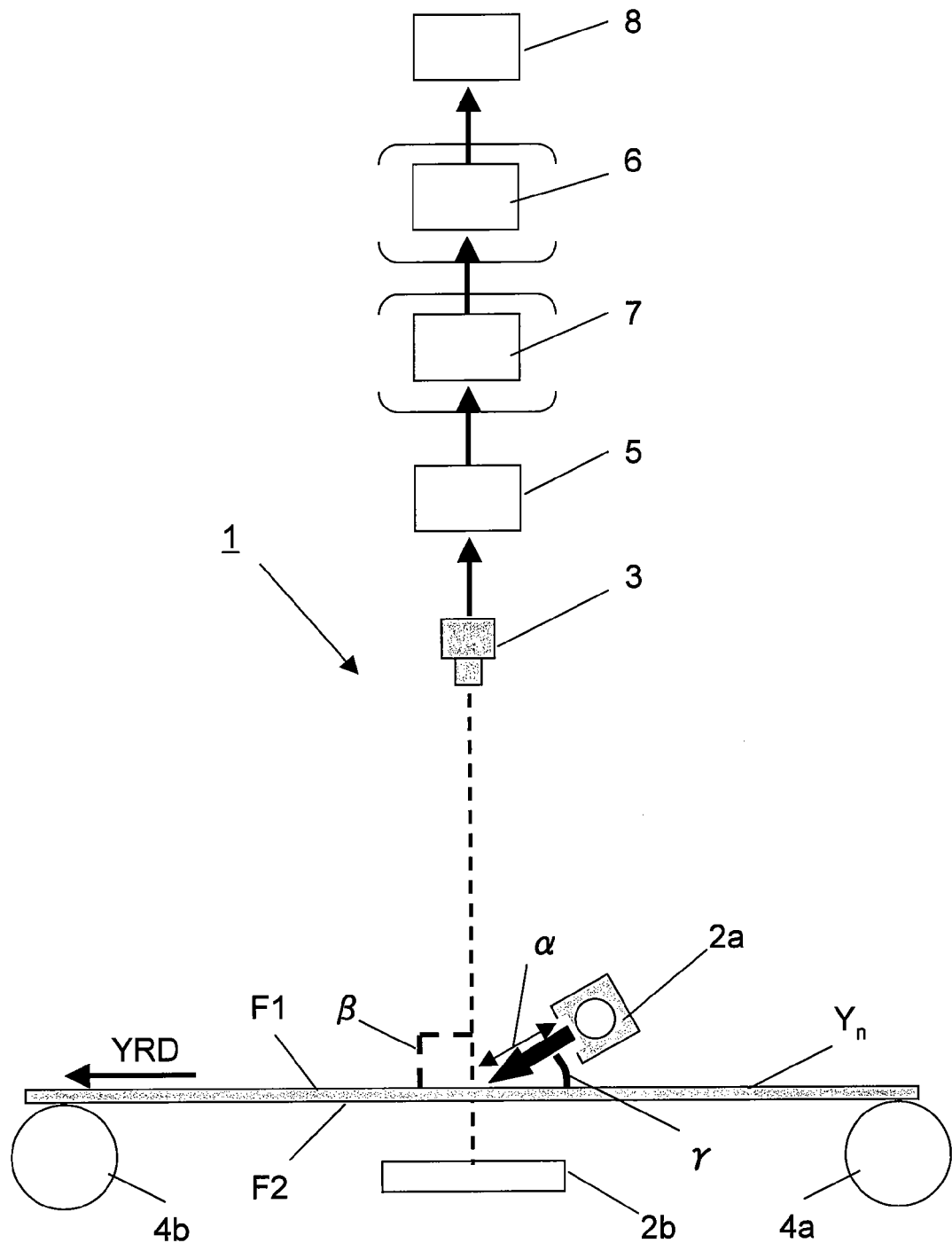
FIG. 1 is a schematic side view showing an embodiment of inspection data acquiring and processing equipment for acquiring and processing inspection data used for carrying out the running yarn inspection method in an embodiment of the invention.

1: inspection data acquiring and processing equipment
2a: first illumination means
2b: second illumination means
3: imaging means
4a, 4b: yarn guide roll
5: first data processing procedure
6: second data processing procedure
7: third data processing procedure
7A, 7B, 7C: profile of pixel values
8: recording means
9: light scattered from a defect
10: fuzz defect
10A, 10B: profile of pixel values 11: a fluff defect existing in a background portion
12: a fluff defect existing in two background portions
13: an added and averaged range in a normal portion to be employed as a master
14: an added and averaged range in a portion to be inspected
15: a bright portion (portion corresponding to a background portion)
16: a dark portion (portion corresponding to a yarn portion)
17: a fall toward a minus peak
18: a rise toward a plus peak
19: vibration of a yarn
20: an example of the method for collecting the profile data concerning contrast in the running direction of yarns
21: another example of the method for collecting the profile data concerning contrast in the running direction of yarns
31: inspection data acquiring and processing equipment
32$a$1, 32$a$2: first illumination means
32$b$1, 32$b$2: second illumination means
33$a$, 33$b$: imaging means
$C_1$ to $C_{n-1}$: yarn clearance (background portion)
$c_1$ to $c_{n-1}$: portion corresponding to a yarn clearance in an image
F1: first face
F2: second face
P3: plus peak
P5: minus peak
$Pc_1$ to $Pc_7$: plus peak (bright portion) (background portion)
$Py_1$ to $Py_8$: minus peak (dark portion) (yarn portion)
$Y_1$ to $Y_n$: yarn (yarn portion)
$y_1$ to $y_n$: portion corresponding to a yarn in an image
YR: yarn row
YRD: yarn running direction
YRF: yarn running plane
α: distance between first illumination means and yarns
β: angle formed between the visual field of imaging means and yarns
γ: angle formed between the illumination light of first illumination means and yarns

DETAILED DESCRIPTION OF THE INVENTION

The yarns to which the running yarn inspection method in an embodiment of the invention can be applied include, for example, synthetic fiber yarns formed of acrylic fibers, polyamide fibers, polyester fibers or aramid fibers and inorganic fiber yarns formed of glass fibers or carbon fibers. The running yarn inspection method in an embodiment of the invention allows the difference between the luminance of the yarn portions and the luminance of the background portions formed between the respectively adjacent yarns to be easily expanded. Therefore, the running yarn inspection method in an embodiment of the invention can be preferably used for inspecting the yarns having low lightness irrespective of whether the low lightness is attributable to the material per se of the yarns or is achieved by any processing such as dyeing. Above all, the method of the invention according to an exemplary embodiment can be especially preferably used for inspecting black carbon fiber yarns.

Each of the yarns to which the running yarn inspection method of the invention can be applied is a bundle comprised numerous continuous filaments and usually comprising about 10 to about 1,000,000 filaments.

The running yarn inspection method of the invention (hereinafter may be referred to as "the method of the invention" as the case may be) can be used in various yarn production processes requiring the identification of yarn defects. As such production processes, the production process of synthetic fibers includes, for example, an oiling step, stretching step and heat treatment step, and the production process of carbon fibers include, for example, a oxidization step and carbonization step. In the case where an intermediate product is sent to a next step, it is preferred that the inspection for finding whether or not yarns have defects and for finding the states of the defects, if any, is performed in the final step in the production process of the intermediate product, and in the case where a product is delivered to a customer, it is preferred that the inspection is performed in the final step in the production process of the product.

The "a plane" of "multiple yarns running in parallel to each other in a plane" in the method of the invention, for example, refers to the plane along the running multiple yarns parallel to each other located between the two yarn guide rolls installed in parallel to each other with a distance kept between the rolls in the running direction, while the multiple yarns run in contact with the two yarn guide rolls. This plane can also be called the yarn running plane. It is preferred for carrying out the method of the invention that the yarn running plane is horizontal but may be curved to some extent owing to the tensions acting on the yarns, the distance between the yarn guide rolls, etc. as the case may be.

The "first face" of "the first face side and the second face side of the yarn running plane" in the method of the invention refers to the face on either side of the yarn running plane, and the other face of the yarn running plane on the side opposite to the side selected for the first face is the second face. In the case where the yarn running plane is substantially horizontal, usually the upper face of the yarn running plane is selected as the first face in view of the relation between the arrangement of a equipment for carrying out the method of the invention and the arrangement of a yarn production equipment.

The illumination means used for illumination from the first face side in the method of the invention (hereinafter referred to as "the first illumination means") is only required to allow uniform illumination of every yarn in the direction crossing the rows of yarns running in parallel to each other, that is, in the transverse direction. It is preferred that the first illumination means can illuminate the every yarn with the difference in light intensity kept within 20% in the transverse direction. If a sufficient light intensity can be scattered from each defect occurring on any yarn, the illumination light is not limited in either intensity or wavelength. It is preferred that the illumination light of the first illumination means has such an intensity that allows the light scattered from each defect occurring on any yarn to enter the imaging means at an illuminance of 0.1 lx·s or more in view of the light reception sensitivity of the imaging means.

As the first illumination means, a fluorescent lamp driven by high frequency power source, metal halide lamp or the like which is linear in the light emitting can be used. Further, an illumination means for guiding the light from a light source such as a halogen or LED by a light guide with multiple optical fibers linearly arranged, or an illumination means for applying light to the end face of a cylindrical rod lens, or an illumination means with a cylindrical lens provided in front, etc. can be used. As the first illumination means, in view of cost and maintainability, it is preferred to use a fluorescent lamp driven by a high frequency power source.

The illumination means used for illumination from the second face side in the method of the invention (hereinafter referred to as "the second illumination means") is only required to be an illumination means capable of providing illumination light that allows the measurement of the light transmitted through the clearances formed between the respectively adjacent yarns, and is not limited in the intensity or wavelength of the illumination light. If the illuminance of the second illumination means is too large, the light intensity entering the imaging means becomes too large. To prevent it, if the incident light intensity from the second illumination means is decreased for example, there arises a problem that the light of the first illumination means reflected/scattered from each defect occurring on any yarn and entering the imaging means becomes extremely small. Further, if light with an illuminance value larger than the saturated exposure of the imaging means enters the imaging means, the accuracy of detecting each defect of a yarn positioned in a background portion may decline as the case may be. Therefore, it is preferred that the intensity of the illumination light of the second illumination means is equal to or lower than that of the first illumination means.

The second illumination means is only required to uniformly illuminate the every yarn in the direction crossing the rows of the yarns running in parallel to each other, that is, in the transverse direction like the first illumination means. It is preferred that the second illumination means can illuminate every yarn with the difference in light intensity kept within 20% in the transverse direction. As the second illumination means, for example, a fluorescent lamp that is linear in the light emitting portion and can be turned on by a high frequency power source can be used like the first illumination means.

Further, if the first illumination means can uniformly illuminate every yarn with the fluctuation in light intensity kept within 20% in the transverse direction, the second illumination means can also be a reflection plate capable of reflecting the illumination light of the first illumination means passing through the clearances formed between the respectively adjacent yarns. The reflection plate used as the second illumination means is preferred, since it requires only a small installation place and allows simple maintenance. The reflection plate is not especially limited if it can reflect the illumination light of the first illumination means and allows the reflected light to enter the imaging means. The reflection plate used can be, for example, a white plate or sheet having a low light transmittance.

The imaging means in the method of the invention refers to a sensor in which light receiving elements (pixels) such as light receiving CCD elements are set up linearly or two-dimensionally for obtaining data concerning contrast. It is preferred that the imaging means is a line sensor in which light receiving elements are set up linearly.

The reasons why the use of a line sensor as the imaging means is preferred are that a line sensor is excellent in the resolution in the transverse direction and allows a wide view field of inspection compared with an area sensor used for obtaining two-dimensional data. For example, in the case where a general area sensor having 2 million pixels (1,600×1,200 pixels) is used for an inspection width with 1,000 mm, the resolution of the sensor in the transverse direction is 1,000÷1,600=0.625 mm at maximum resolution. However, in the case where a line sensor having 7,500 pixels almost equal in cost is used, the resolution is 1,000÷7,500=0.133 mm. That is, a resolution of about 4.7 times can be obtained. Therefore, a line sensor allows a range of 4.7 times to be simultaneously inspected, compared with an area sensor having the same resolution.

In the case where the inspection width of numerous yarns to be inspected by the method of the invention is wide in the transverse direction, it is necessary to use multiple sensors. If the number of yarns to be inspected simultaneously is larger, less line sensors are required than area sensors, to assure an advantage in view of cost. For example, in the abovementioned case, if it is assumed to measure a range of 1,000 mm at a required resolution of 0.1 mm, the number of area sensors having 2 million pixels (1,600×1,200 pixels) required is (1,000÷0.1)÷1,600=6.25. That is, at least seven sensors are necessary. However, the number of line sensors having 7,500 pixels required is (1,000÷0.1)÷7,500=1.33. That is, only two sensors are required.

It is preferred that the number of pixels of a line sensor is 2,000 pixels or more to respond to the abovementioned inspection of numerous yarns set up in an inspection range wide in the transverse direction. It is preferred that the light reception sensitivity of a line sensor is about 10 to about 1,000 V/lx·s so that the sensor can receive the light scattered from each defect of any yarn at the time of measurement. Particularly, sensors produced by Nippon Electro-Sensory Devices Co., Ltd., Takenaka System Co., Ltd., etc. can be used.

To be strict, a line sensor does not simultaneously inspect the inspection range, since it images one yarn by one in the pixel direction sequentially. However, one scanning time period of a general line sensor is a short time period of 50 to 200 µs, and even if this time period is expressed as being simultaneous, no practical problem occurs. Therefore, in this description, it is explained that multiple yarns are simultaneously inspected.

In the method of the invention according to an exemplary embodiment, the first illumination means and the imaging means for imaging multiple yarns are installed on the first face side, and the second illumination means is installed on the second face side. In this constitution, the illumination light from the second illumination means is intercepted by the yarns, to expand the difference between the luminance of the yarn portions and the luminance of the background portions, for allowing the yarn widths and the lightness values in the transverse direction of yarns to be measured accurately.

The method of the invention according to an exemplary embodiment further has a step of processing the received light data obtained by the imaging means, by a data processing means and a step of recording some or all of the data obtained by the data processing means, into a recording means with the lapse of time.

The data processing by the data processing means is performed by a first data processing procedure, a second data processing procedure and/or a third data processing procedure. The first data processing procedure, second data processing procedure and third data processing procedure refer to the following data processing procedures.

First Data Processing Procedure:

A data processing procedure for specifying the positions of yarns from the received light data obtained by the imaging means and calculating each yarn width specified from the positions of the yarns and the lightness values in the transverse direction of each yarn.

Second Data Processing Procedure:

A data processing procedure for comparing the data obtained by the first data processing procedure with a preset threshold value.

Third Data Processing Procedure:

A data processing procedure to perform adding and averaging calculations for a preset number of scanned data sets obtained from consecutive measurements in the running direction of the yarns by the first data processing procedure, followed by calculating the differences between the sums and calculating the differences between the averages of the data in the consecutive data sets.

The received light data obtained by the imaging means refers to the data concerning contrast in the range measured by the sensor.

The first data processing procedure obtains the data concerning contrast obtained by the imaging means, as a profile of pixel values concerning the positions of light receiving elements (pixels) and lightness values, then distinguishes the yarn portions from the background portions in the lightness pattern of the profile, subsequently specifies the positions of yarns from the pixel positions of the yarn portions, and calculates the lightness values at the specified positions of yarns in the transverse direction of yarns.

Figure 7:
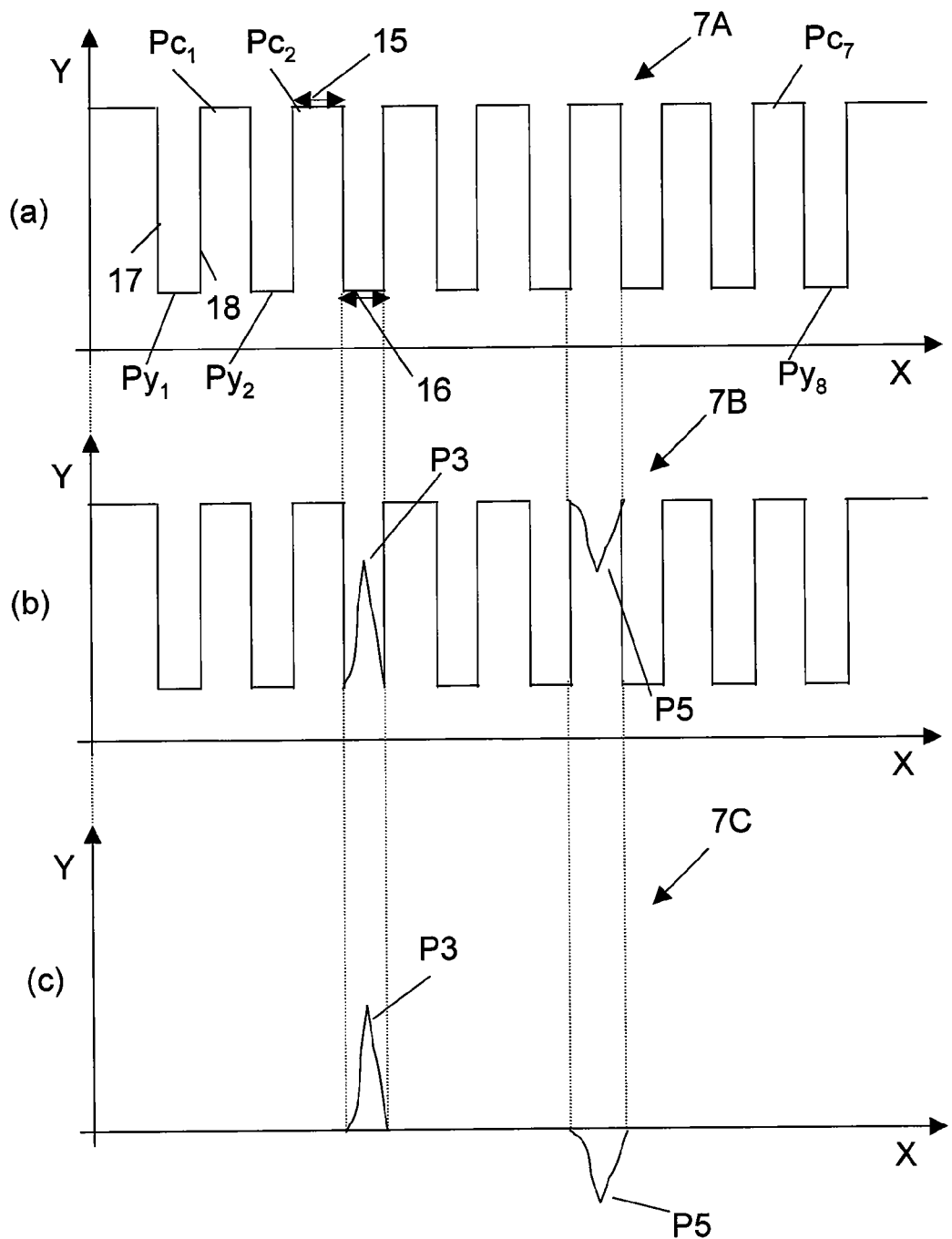
FIG. 7 illustrates graphs typically showing examples of the profiles obtained by processing the image obtained by the inspection data acquiring and processing equipment shown in FIG. 1.

The particular procedure will be explained using FIG. 7. The horizontal axis X in the three graphs (a), (b) and (c) arranged vertically in FIG. 7 represents pixel positions, and the vertical axis Y represents pixel values. The detail will be described later. The graph of FIG. 7 (a) is a profile of pixel values in the transverse direction in the case where the every yarn does not have any defect, namely are completely normal. The graph of FIG. 7 (b) is a profile of pixel values in the transverse direction in the case where some yarns have defects. The profile of pixel values in the transverse direction is used for specifying the positions of yarns and yarn widths from the lightness pattern and pixel positions of the received light data (hereinafter may be referred as the primary data) obtained by the first data processing procedure.

The second data processing procedure compares the primary data obtained by the first data processing procedure with a preset threshold value. The threshold value is used in such a manner that when the quantity of a lightness change or the number of pixels of the dark portion showing each yarn width is larger or smaller than the threshold value, it is determined that the yarn concerned has a defect. The threshold value is set, for example, on the basis of the difference between the lightness of a normal portion and the lightness of a defect speck obtained by measuring the normal portion and the defect speck prepared by an ideal model or obtained by actual sampling.

As the threshold value, it may be necessary to set different threshold values for respective types of yarns to be produced, or setting one threshold value only may be enough. There may also be a case where it is necessary to use multiple threshold values selectively. For execution of the second data processing procedure, it is preferred to pre-arrange a storage device such as a personal computer as a threshold value storing means.

If the second data processing procedure is used in addition to the first data processing procedure, the existence of a bright speck with a lightness value larger than a predetermined threshold value or the existence of a dark speck with a lightness value smaller than a predetermined threshold value can be identified, and on the basis of it, the occurrence of a defect on a yarn can be determined. In addition, on the basis of the combination comprising the first data processing procedure and the second data processing procedure, the position at which a defect on a yarn occurs can be specified in the transverse direction within the range of sensor measurement from the position of the light receiving element with a lightness value larger or smaller than the threshold value.

In the case where a defect of a yarn appears in a portion between yarns, in other words, in a background portion, the defect is recognized as a dark speck. In this case, a lightness value smaller than a threshold value can be determined to indicate the existence of a defect, and thus the defect can be detected. Further, in the case where a defect exists in a yarn portion, the defect is recognized as a bright speck. In this case, a lightness value larger than a threshold value different from the aforementioned threshold value can be determined to indicate the existence of a defect, and thus the defect can be detected.

In the case where the number of pixels in the transverse direction of yarns at the position of a yarn corresponding to the width of the yarn, calculated by the first data processing procedure, is larger or smaller than a predetermined threshold value, it can also be determined that the width of the yarn is defective. Thus, whether the width of a yarn is normal or abnormal can also be detected.

In the third data processing procedure, the primary data of a preset number of scanning times obtained in the running direction of yarns by the first data processing procedure are added and averaged, and such added and averaged data are consecutively obtained with the lapse of time, and further the difference between the added and averaged data of one preset number of scanning times and the added and averaged data of the next preset number of scanning times is obtained one after another consecutively.

In this case, the running direction of yarns refers to the running direction in which multiple yarns run in parallel to each other in a plane. The running direction of yarns in the yarn production equipment means the direction in which yarns run in the location to which the method of the invention is applied.

The preset number of scanning times refers to the number of scanning times decided by the line (running yarn) speed, the scanning period of the imaging means, the size of the defect to be detected on a yarn and necessary resolution. For example, if the line speed is 20 m/min, a line sensor is used as the imaging means, the scanning period of the line sensor is 0.1 ms, the size of the defect to be detected in the line running direction is 1 mm, and the required resolution is $\frac{1}{3}$ of the defect to be detected, then the yarns and the defect to be detected move by $\frac{1}{30}$ mm during one time of scanning by the line sensor. Therefore, the number of scanning times permitted at the time of addition is up to 10 times. If the number of scanning times at the time of addition is too small, a sudden change, for example, the mechanical vibration of a line sensor or a yarn may be remarkably identified as a lightness change. Therefore, it is usually preferred to scan 2 times or more.

Addition refers to adding the lightness data of a preset number of scanning times of a line sensor at each pixel position, and averaging refers to dividing the value of the sum obtained by the addition, by the number of scanning times.

Obtaining such added and averaged data consecutively with the lapse of times means that added and averaged data is obtained from the lightness data of a preset number of scanning times of the line sensor, that added and average data is obtained from the lightness data of the next preset number of scanning times of the line sensor, without taking any time interval, and that this operation is repeated.

Obtaining the difference refers to obtaining the difference between the added and averaged data of one preset number of scanning times and the added and averaged data of the next preset number of scanning times one after another consecutively for each light receiving element.

If the third data processing procedure is used in addition to the first data processing procedure, the effects of line sensor vibration and yarn vibration can be decreased, and only the changes of lightness can be monitored, allowing attention to be paid only to the places where changes occur.

It is also possible to use both the second data processing procedure and the third data processing procedure in addition to the first data processing procedure. In this case, the effects of line sensor vibration and yarn vibration can be decreased, and only the quantity of lightness change can be compared with the threshold value. Therefore, defects (disorders) of yarns can be detected more accurately, and the positions where defects occur can also be easily specified.

In the case where an area sensor is used as the imaging means, the imaging elements are set up two-dimensionally. Therefore, the data concerning contrast obtained by one time of scanning by the area sensor and the primary data obtained by the first data processing procedure are temporally continuous two-dimensional data. Therefore, if the two-dimensional data obtained by one time of scanning is stored in a storage device such as a personal computer, and the two-dimensional data of the defects to be detected is divided in the same direction as the pixel direction of the line sensor in the storage device, then the data can be handled like the one-dimensional data obtained by a line sensor. In this case, as in the case of a line sensor, the third data processing procedure can be executed.

The method of the invention according to an exemplary embodiment has a step of recording some or all of the data obtained by the abovementioned data processing procedure into a recording means with the lapse of time. In this case, recording with the lapse of time means to record the time of detecting a defect (disorder) of a yarn and the position of the defect and/or the yarn number whenever a defect is detected. If such a recording medium is used, which yarn and what portion of the yarn have been found to have a defect (disorder) can be specified, and the defect data of every yarn or every yarn package can be recorded.

If only the data portions including yarns having defects are extracted from the temporally continuous lightness data obtained by the first data processing procedure and are recorded as two-dimensional data of an image concerning contrast into the recording means, the types, forms, etc. of the defects can be easily confirmed later.

If the two-dimensional data concerning contrast recorded in the recording means is used to prepare a profile concerning contrast in the running direction of the yarn corresponding to each position where a lightness change occurs, whether the lightness change obtained by the third data processing procedure is caused by a defect formed on a yarn or by vibration of the yarn can be distinguished in reference to whether the subsequent lightness changes are periodic in the running direction of the yarn.

It rarely occurs that one or two yarns among the numerous yarns running in parallel to each other suddenly vibrate, being caused by any process failure such as a trouble of a yarn winder or a worker's touch of the yarn(s), etc. If a yarn vibrates, any lightness change is highly likely to occur in the data obtained by the third data processing procedure. In this case, the vibration of a yarn is detected as a defect like fluff or fuzz.

Therefore, in the case where any occurring vibration of a yarn is desired to be distinguished from a defect and to be recorded with the lapse of time or in the case where it is necessary to distinguish the vibration of a yarn from a defect, required is a processing procedure for automatically distinguishing whether any lightness change found in the data obtained by the third data processing procedure is based on the vibration of a yarn or based on a defect such as fluff.

In the case where the vibration of a yarn occurs, lightness changes occur in the running direction of the yarn periodically for a long time period unlike a defect such as fluff. Therefore, if a profile of lightness in the running direction of the yarn corresponding to the position where the lightness change occurs is prepared with respect to the lightness change in the data obtained by the third data processing procedure, with an intention to determine whether the subsequent lightness changes are periodic, then whether the change is based on the vibration of the yarn or based on a defect can be distinguished.

If an alarm means for reporting the occurrence of a defect (disorder) or the defect position is installed, the defect can be responded to as soon as it occurs, for example, the defect can be confirmed and removed early, and the yield of producing yarns in the yarn production process can be enhanced.

A process disorder can be detected in response to the number of occurring defects, and if the production process is changed or adjusted accordingly, process control can be performed. Further, the removal of occurring defects and the early change or adjustment of the production process allows yarns having higher quality to be produced. Furthermore, the defect data of each yarn obtained can be used to determine the appearance quality of the yarn, or to specify the defective portions of a yarn package. For example, if the defect data of a yarn package is attached to the yarn package when the yarn package is delivered to a customer, defects can be removed based on the defect data, for example when the yarn is unwound from the package. A defectless yarn package is ideal, but the defect data attached to a yarn package can be quality assurance as the case may be.

The running yarn inspection method of the invention according to exemplary embodiments is explained below in reference to the drawings.

Figure 2:
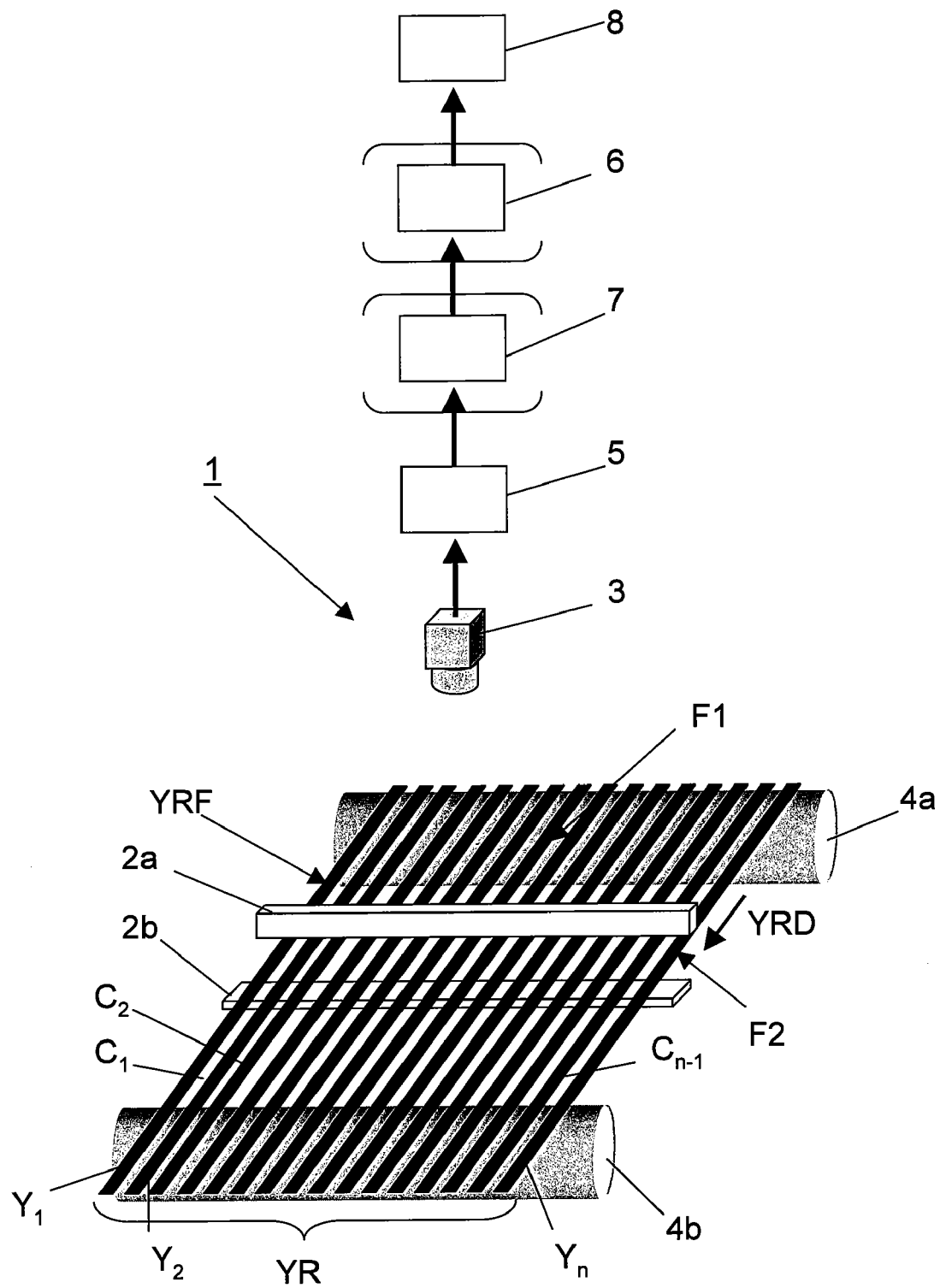
FIG. 2 is a schematic perspective view of the inspection data acquiring and processing equipment shown in FIG. 1.

FIG. 1 is a schematic side view showing an embodiment of inspection data acquiring and processing equipment for acquiring and processing the inspection data used for carrying out the running yarn inspection method in an embodiment of the invention. FIG. 2 is a schematic perspective view of the inspection data acquiring and processing equipment shown in FIG. 1.

In FIGS. 1 and 2, an inspection data acquiring and processing equipment 1 has two yarn guide rolls 4a and 4b positioned in parallel to each other with a distance kept between them. Numerous yarns $Y_1$ to $Y_n$ run in the direction indicated by arrow YRD in parallel to each other with clearances $C_1$ to $C_{n-1}$ kept between the respectively adjacent yarns in contact with the yarn guide rolls 4a and 4b. The numerous yarns $Y_1$ to $Y_n$ form yarn rows YR. The yarn rows YR in the portion between the yarn guide rolls 4a and 4b form a yarn running plane YRF. The every yarn is positioned in the yarn running plane YRF, namely, in a plane.

On the side of a first face F1 of the yarn running plane YRF, a first illumination means 2a is installed, and on the side of a second face F2, a second illumination means 2b is installed. An imaging means 3 is installed on the side of the first face F1 at a location not receiving the light regularly reflected from the every yarn. In FIG. 1, the first face F1 is the upper face of the yarn running plane YRF.

The data signals obtained by the imaging means 3 are converted into the primary data concerning contrast by a first data processing procedure 5. Subsequently a second data processing procedure 6 or a third data processing procedure 7 is performed, or the processing results of the third data processing procedure 7 are supplied to the second data processing procedure 6, in order to ensure that desired comparing or processing operations are carried out by the appropriate procedures. Some or all of the results for the every yarn are recorded into a recording means 8, and the records are used for quality control of the every yarn, etc.

The positional relationship among the every yarn, the first illumination means 2a, the imaging means 3 and the second illumination means 2b are explained below. In the case where the imaging means 3 is a line sensor, it is preferred to install the line sensor to keep the pixel direction thereof in the direction perpendicular to the running direction YRD of the respective running yarns (in the transverse direction). The distance between the every yarn and the imaging means 3 can be univocally decided on the basis of the angle of view decided by the imaging means 3 and the lens, the number of pixels of the imaging means, inspection range and required resolution.

In FIG. 1, it is preferred that the distance between the first illumination means 2a and the every yarn indicated by symbol α is within 500 mm, since a longer distance lowers the intensity of the illumination light, to lower the detection accuracy. The positional relationship between the first illumination means 2a and the imaging means 3 is not especially limited, if the illumination light of the first illumination means 2a regularly reflected by the every yarn does not directly enter the imaging means 3. If the visual field of the imaging means 3 is virtually perpendicular to the every yarn as shown by symbol β in FIG. 1, and if the angle formed between the illumination light of the first illumination means 2a and the every yarn is 10 to 40° as shown by symbol γ in FIG. 1, then defects such as fluffs and fuzz formed on the every yarn can be accurately detected. The position of the second illumination means 2b is not especially limited, if it is on the extension of the visual field of the imaging means 3 and if the illumination light required for measurement can enter the imaging means 3.

The yarn inspection principle in the method of the invention according to an exemplary embodiment is explained below using drawings, together with the processings of the first data processing procedure 5, the second data processing procedure 6 and the third data processing procedure 7.

Figure 4:
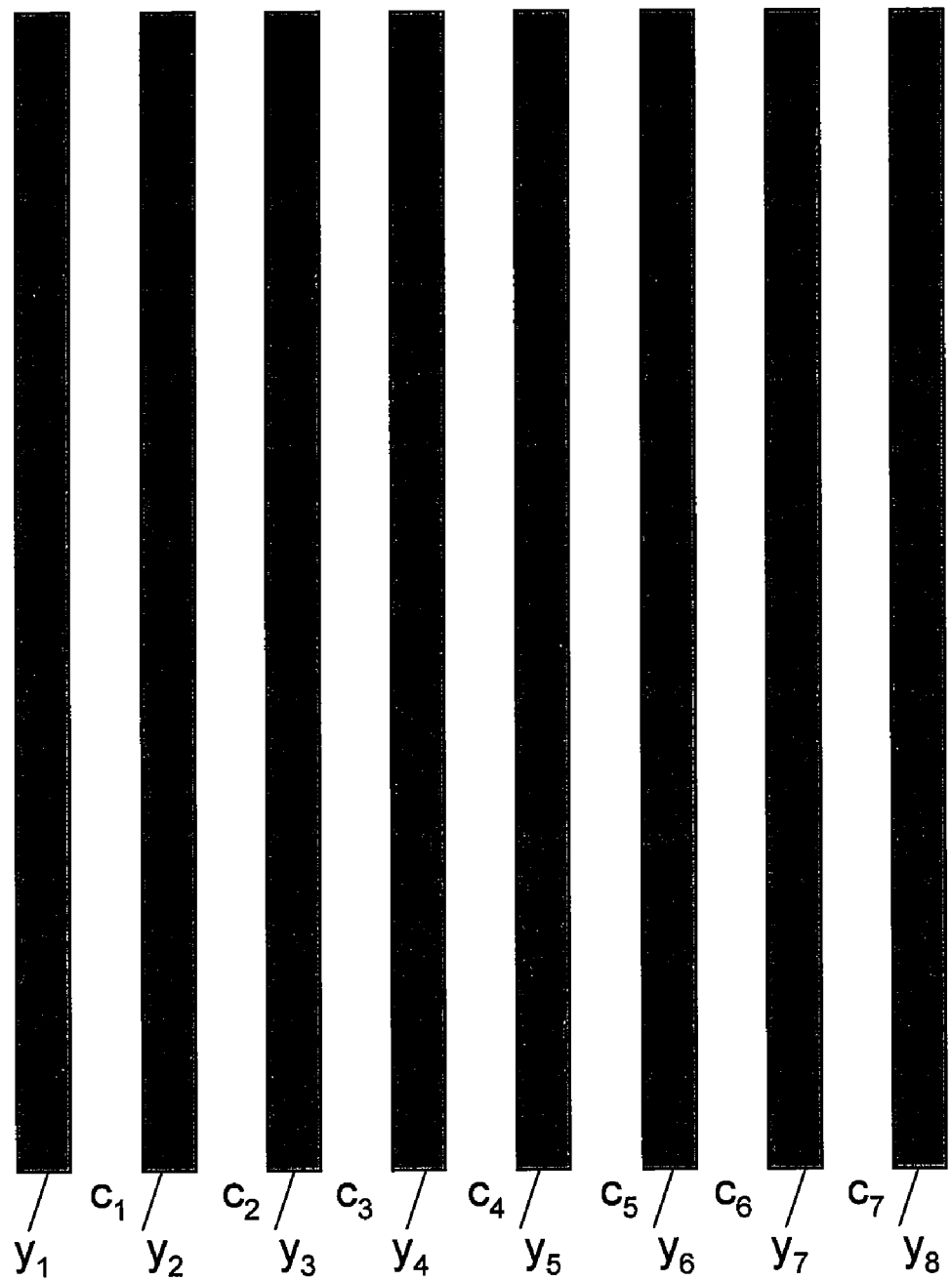
FIG. 4 is an exemplary diagram of an image obtained by imaging a case where numerous running yarns are respectively normal yarns.

At first, the processing of the first data processing procedure 5 will be explained. If defectless normal yarns are imaged by the imaging means 3, especially in the case where the imaging means 3 is a line sensor, and if the imaged results of respective predetermined numbers of scanning times are connected continuously with the lapse of time, then a two-dimensional image as shown in FIG. 4 or data rows corresponding to the two-dimensional image can be obtained. Meanwhile, for the convenience of explanation, obtaining a two-dimensional image is explained, but obtaining the image is not necessarily essential, and data rows corresponding to the two-dimensional image, a continuous pattern of the data rows or the like can also be used. Obtaining a two-dimensional image including these modes is explained below as obtaining a two-dimensional image.

As shown in FIG. 4, the light from the second illumination means 2b reaching the yarn portions $Y_1$ to $Y_8$ is intercepted by the yarn portions $Y_1$ to $Y_8$ and does not enter the imaging means 3. Therefore, in the imaging means 3, the portions $y_1$ to $y_8$ corresponding to the every yarn become dark. On the other hand, the light from the second illumination means 2b reaching the yarn clearances $C_1$ to $C_7$ formed between the respectively adjacent yarns passes through the yarn clearances and enters the imaging means 3 as transmitted light. Therefore, in the imaging means 3, the portions $c_1$ to $c_7$ corresponding to the yarn clearances become bright. These yarn clearances become background portions, and the imaging means 3 provides an image in which the background portions and the yarn portions can be clearly distinguished.

Figure 5:
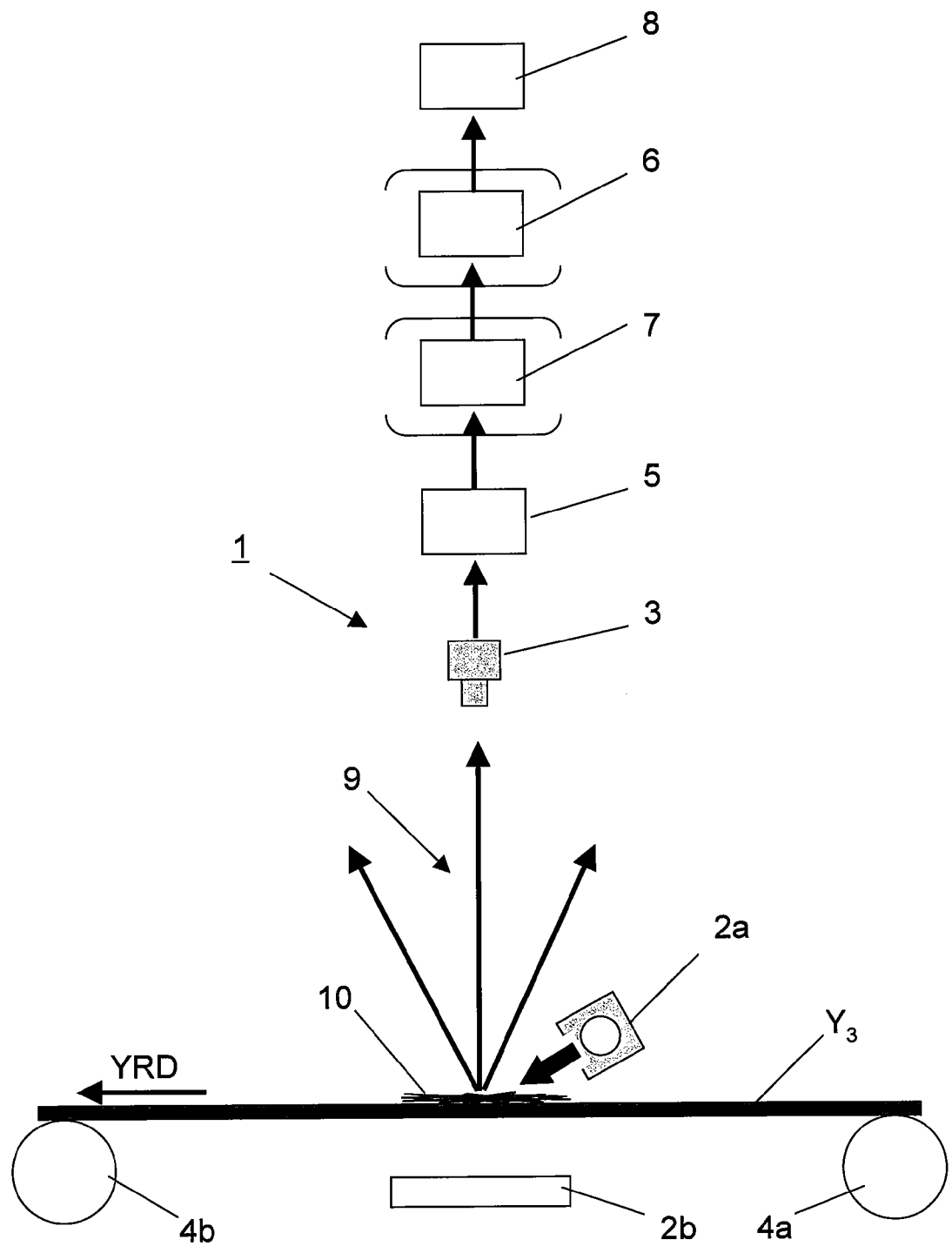
FIG. 5 is a schematic side view of the inspection data acquiring and processing equipment shown in FIG. 1 in a typical case where a yarn having a fuzz (defect) thereon has come to the inspection position.

FIG. 5 typically shows a case where a fuzz defect occurs on the yarn $Y_3$. In FIG. 5, in the case where a fuzz defect 10 occurs on the yarn $Y_3$, the fuzz defect 10 scatters the illumination light from the illumination means 2a, and the scattered light 9 enters the imaging means 3. The image obtained including the light 9 scattered from the fuzz defect 10 by the imaging means 3 includes a speck indicated by the same symbol 10 in FIG. 6 as the defect 10. That is, the speck on the yarn that is a dark portion becomes a bright speck in the image since the light 9 scattered from the fuzz defect 10 enters the imaging means 3.

Figure 6:
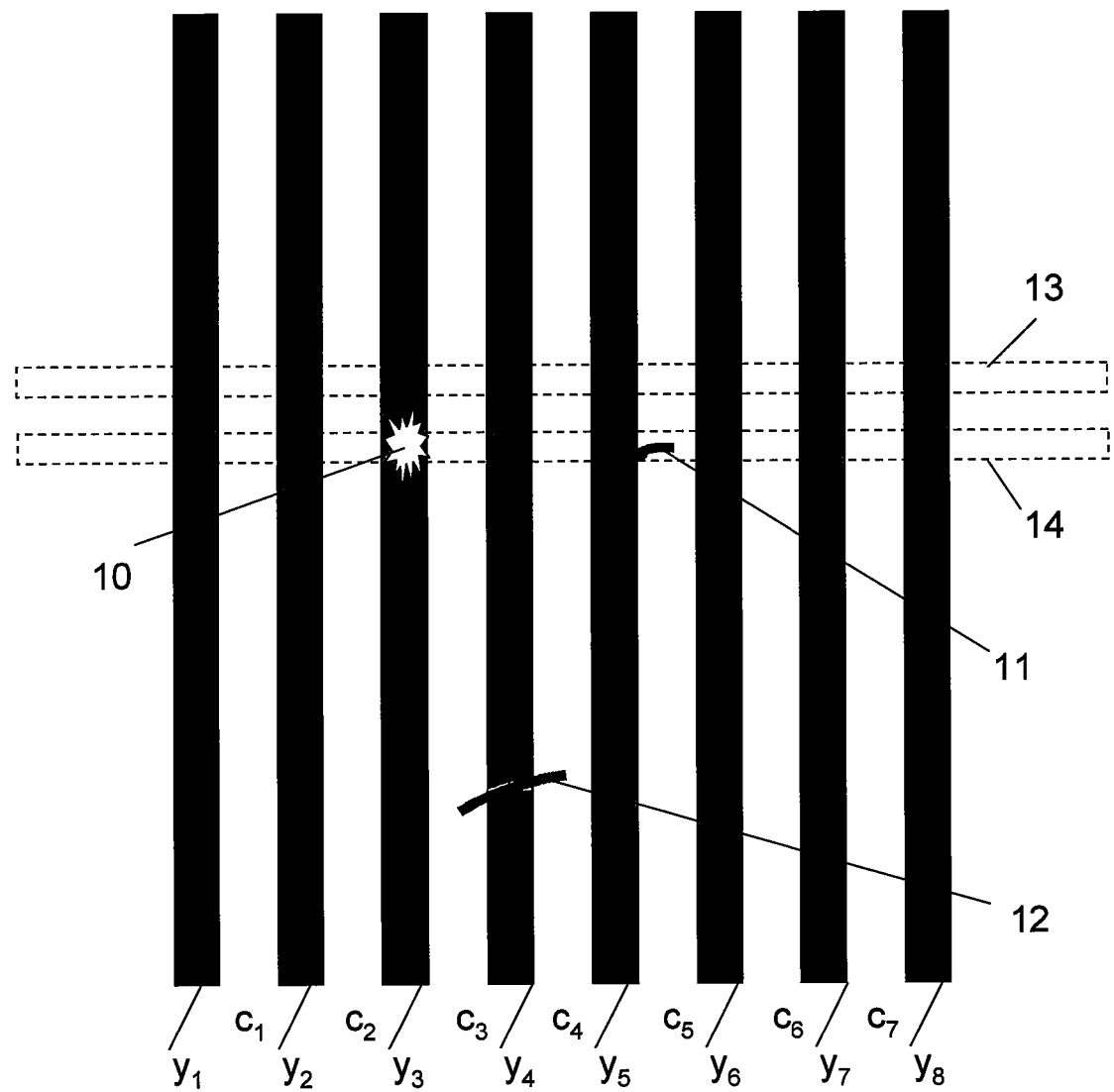
FIG. 6 is an exemplary diagram of an image obtained by imaging a case where three yarns respectively having different defects appear in the yarn running state shown in FIG. 4.

In the case where a piece of fluff is formed in the yarn clearance $C_5$, a fluff defect indicated by symbol 11 in FIG. 6 appears in the image. That is, a speck in the background portion that is a bright portion owing to the second illumination means becomes a dark speck in the image, since the fluff defect 11 formed in the yarn clearance $C_5$ intercepts the illumination from the second illumination means. Further, in the case where a piece of fluff 12 mounted on the yarn $Y_4$ and extending into the yarn clearances $C_3$ and $C_4$ (background portions) occurs, the fluff defect indicated by symbol 12 in FIG. 6 appears in the image. That is, the fluff defect 12 appears as a bright fragment of a speck on the yarn portion and as dark fragments of the speck in the background portions in the image.

Therefore, for example in FIG. 6, in a range 13 in the direction crossing the yarn rows YR, if the data of a predetermined number of scanning times obtained from the imaging means 3 are added and averaged according to the method explained before, a profile 7A having pixel values in the transverse direction as shown in FIG. 7 (a) can be obtained. In FIG. 7 (a), the vertical axis Y represents pixel values (lightness values), and the horizontal axis X represents pixel positions (positions in the transverse direction). The profile 7A has inverse peaks $Py_1$ to $Py_8$ (hereinafter referred to as minus peaks) having a low pixel value corresponding to the yarn portions that are dark portions compared with the background portions.

In FIG. 7 (a), for example, the fall 17 and the rise 18 of the minus peak $Py_1$ are borders between a yarn portion and a yarn clearance (background portion). Further, in the range 14 of FIG. 6 including the fuzz defect 10 on a yarn, if the data of a given number of scanning times obtained from the imaging means 3 are added and averaged, a profile 7B shown in FIG. 7 (b) can be obtained. That is, compared with the profile 7A of FIG. 7 (a), since the fuzz defect 10 on a yarn that is a dark portion becomes a bright speck, a plus peak P3 appears at the bright speck corresponding to the fuzz defect in the profile 7B. Further, the fluff defect 11 in a background portion that is a bright portion becomes a dark speck, and in the profile 7B, a minus peak P5 appears at the dark speck corresponding to the fluff defect.

In the profile 7A shown in FIG. 7 (a), the bright portions 15 ($Pc_1$ to $Pc_7$) of the profile 7A correspond to background portions, and the dark portions 16 ($Py_1$ to $Py_8$) having bottom peaks in the profile 7A correspond to running yarns. Therefore, if the pixel positions of the peaks are specified, the positions of the running yarns can be specified. Further, if the number of pixels of the dark portion of a peak is calculated at the position of a running yarn, the width of the running yarn can also be calculated, since the distance per pixel can be univocally decided by the visual field of the camera and the number of pixels. Furthermore, if numbers are given to the minus peaks $Py_1$ to $Py_8$ of the profile 7A shown in FIG. 7 (a) beforehand, the number of the yarn at which a defect occurs can be specified. Moreover, if the positions of yarns are specified with numbering, the width(s) of a specific or multiple running yarns can be monitored at given time periods of measurement.

If the borders between dark portions corresponding to yarn portions and bright portions corresponding to background portions are clearer in an image, the widths of yarns can be more accurately measured. Therefore, it is preferred that the second illumination means 2b is used to enlarge the difference between the luminance of the background portions and the luminance of the yarn portions, for clarifying the borders.

The processing of the second data processing procedure 6 is explained below. In the second data processing procedure 6, the primary data obtained by the first data processing procedure 5 is compared with a predetermined threshold value. For example, in the profile 7A of FIG. 7 (*a*) and the profile 7B of FIG. 7 (*b*), when a pixel value is larger or smaller than the predetermined threshold value, a defect can be determined, or when the number of pixels of a yarn portion expressing the yarn width calculated by the first data processing procedure 5 is larger or smaller than the predetermined threshold value, a yarn width failure can be determined.

The processing of the third data processing procedure 7 is explained below. The third data processing procedure 7 is used to extract only a portion where each lightness change occurs, as a pixel value peak. Particularly, the difference between the data obtained by adding and averaging the data of a predetermined number of scanning times in the imaging means 3 obtained by the first data processing procedure 5 and the data obtained by adding and averaging the data of the next predetermined number of scanning times is obtained. For example, in the case where the difference as mentioned above is obtained, if both the primary data concerned with a predetermined number of scanning times and the primary data concerned with the next predetermined number of scanning times can be expressed by profiles 7A as shown in FIG. 7 (*a*), a peak-less flat profile can be obtained. On the other hand, in the case where either of the profiles is a profile 7B as shown in FIG. 7 (*b*) because of defects occurring in yarns, a profile 7C having a plus peak P3 and a minus peak P5 at the defect occurrence positions as shown in FIG. 7 (*c*) can be obtained as the difference.

In the case where a defect appears as a bright speck as indicated by symbol 10 of FIG. 6 in the image, the profile 7B is obtained as shown in FIG. 7 (*b*), and in the profile 7C of the difference, a plus peak P3 appears at the bright speck corresponding to the defect 10. However in the case where a defect appears as a dark speck as indicated by symbol 11 of FIG. 6 in the image, the dark speck appears in the background portion that is a bright portion, compared with the profile 7A showing normal yarns. Therefore, in the profile 7B of the difference, a minus peak P5 appears at the dark speck corresponding to the defect 11. A peak in the profile of the difference is a plus peak if the defect appears as a bright speck and is a minus peak if the defect appears as a dark speck. However, an absolute value can also be employed in the comparison with a threshold value by the second data processing procedure 6, so that both the defects appearing as bright and dark specks can be converted into plus peaks. Further, both a plus threshold value and a minus threshold value can also be established for processing.

According to the detection principle as explained above, the profile obtained by adding and averaging the data of a predetermined number of scanning times is employed as a master profile, and the profile obtained by adding and averaging the data of the next predetermined number of scanning times is employed as a profile to be inspected. After completion of a series of processing, the aforementioned profile to be inspected is newly employed as a master profile, and the profile obtained by adding and averaging the data of the second next predetermined number of scanning times is employed newly as a profile to be inspected. Such processing can be continuously performed to perform continuous inspection of running yarns.

In the combination of the abovementioned data processing procedures, it is preferred to use all the first data processing procedure, the second data processing procedure and the third data processing procedure, for such reasons that since the effects of imaging means vibration, yarn vibration, etc. can be decreased, the value of each lightness change only can be compared with a threshold value, to allow more accurate detection of defects, and that the positions where defects or disorders occur can also be easily specified. Meanwhile, a combination of the first data processing procedure and the second data processing procedure, or a combination of the first data processing procedure and the third data processing procedure is also possible.

The data concerning defects obtained by the above-mentioned data processing procedures can be recorded into the recording means 8 with the lapse of time.

If only the data portions including yarns having defects are extracted from the continuous lightness data obtained by the first data processing procedure and are recorded as two-dimensional data of an image concerning contrast into the recording means 8, the types, forms, etc. of the defects can be easily confirmed later.

If the yarn defect data recorded in the recording means 8 is used for process control, the occurrences of process disorders can be detected early and the process can be improved. Further, the yield of yarn production can be enhanced and yarns having higher quality can be produced.

The following explains the procedure for distinguishing whether a lightness change obtained by the third data processing procedure is caused by a defect occurring on a yarn or by the vibration of the yarn, by using the two-dimensional data concerning contrast recorded in the recording means 8.

Figure 8:
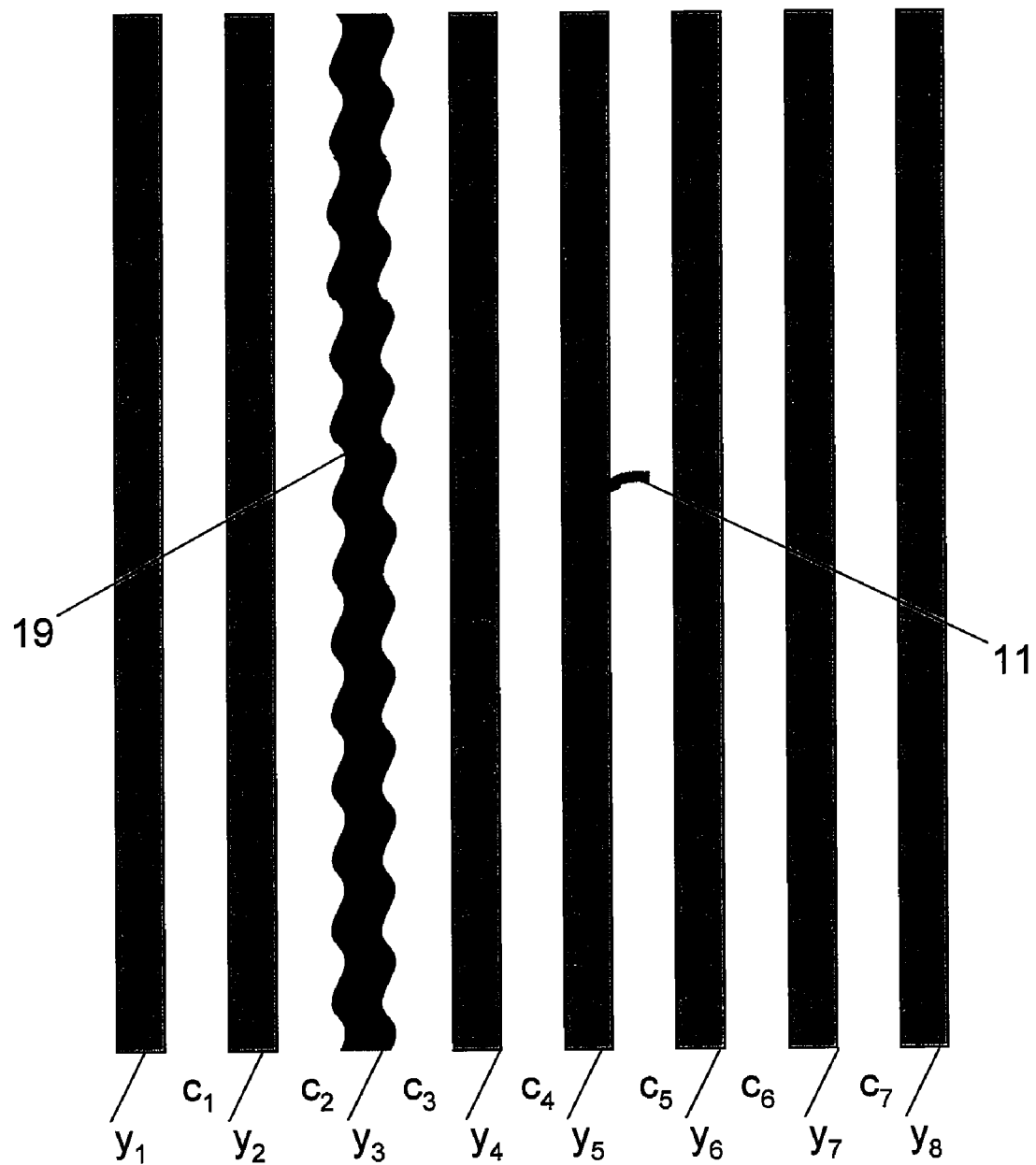
FIG. 8 is an exemplary diagram of an image obtained by imaging a situation wherein one yarn vibrates while another yarn has a fluff defect projecting toward an adjacent yarn in the yarn running state shown in FIG. 4.

FIG. 8 typically shows an image where a yarn $Y_3$ vibrates. As shown in FIG. 8, in the case where the vibration 19 of the yarn $Y_3$ occurs, many lightness changes $y_3$ occur near the vibrating yarn $Y_3$ in the data obtained by the third data processing procedure, and they are recorded in the recording means 8 as the occurrences of many pieces of fluff or other defects. Therefore, any data processing procedure for distinguishing the occurrence of vibration 19 of the yarn $Y_3$ from the occurrences of defects such as fluff 11 of FIG. 8 is necessary.

Figure 9:
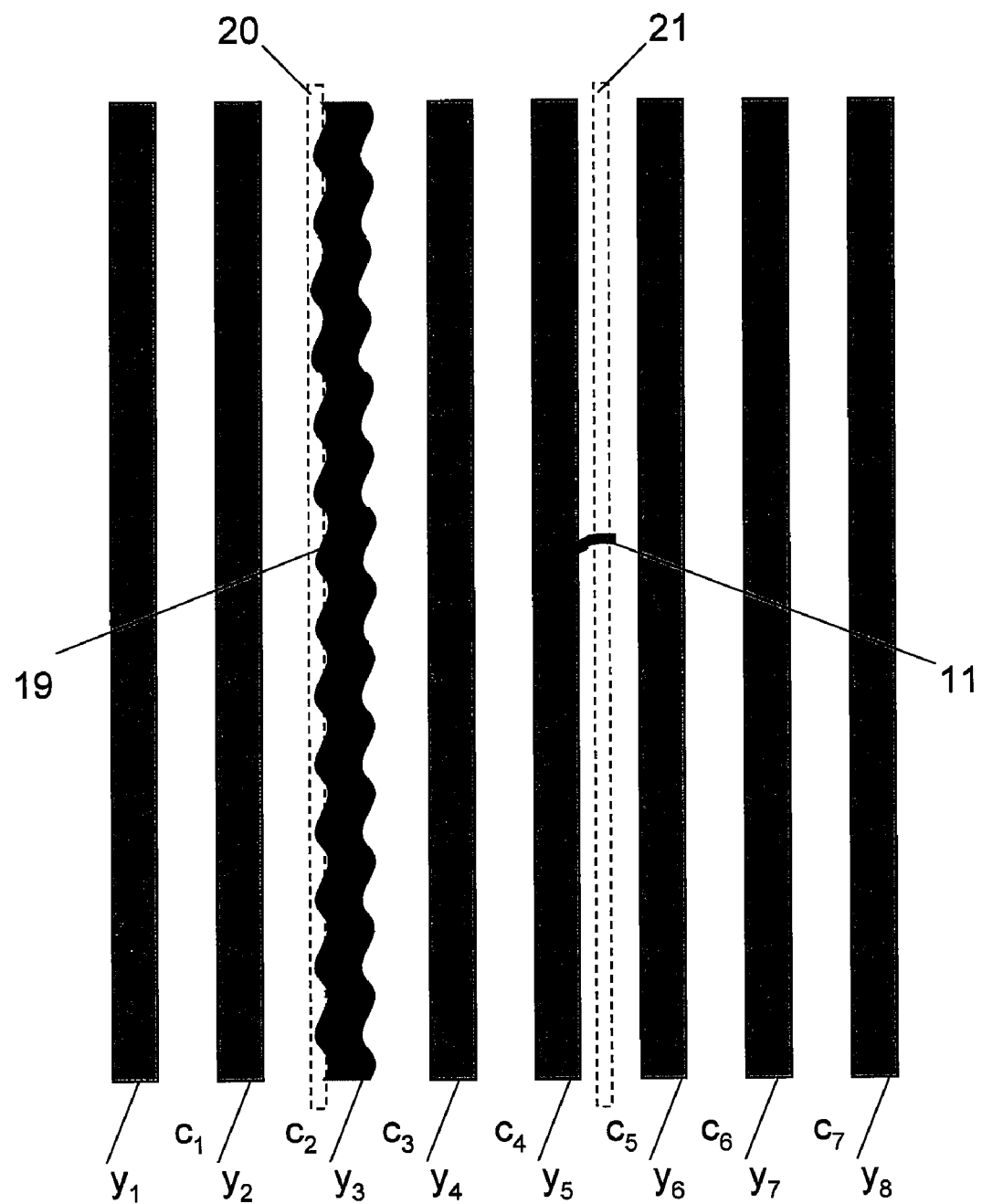
FIG. 9 is an exemplary diagram of the image shown in FIG. 8, wherein a method for determining the vibration of a yarn in distinction from the fluff defect of another yarn shown in FIG. 8 is depicted additionally.

In the method of the invention according to an embodiment, in the case where the quantity of a lightness change obtained by the third data processing procedure is larger than the threshold value set by the second data processing procedure, only the continuous time-series lightness data including the portion where the lightness changes $y_3$ occur among the lightness data obtained by the first data processing procedure is recorded into the recording means 8 as two-dimensional image data, for example, as typically shown in FIGS. 8 and 9.

Figure 10:
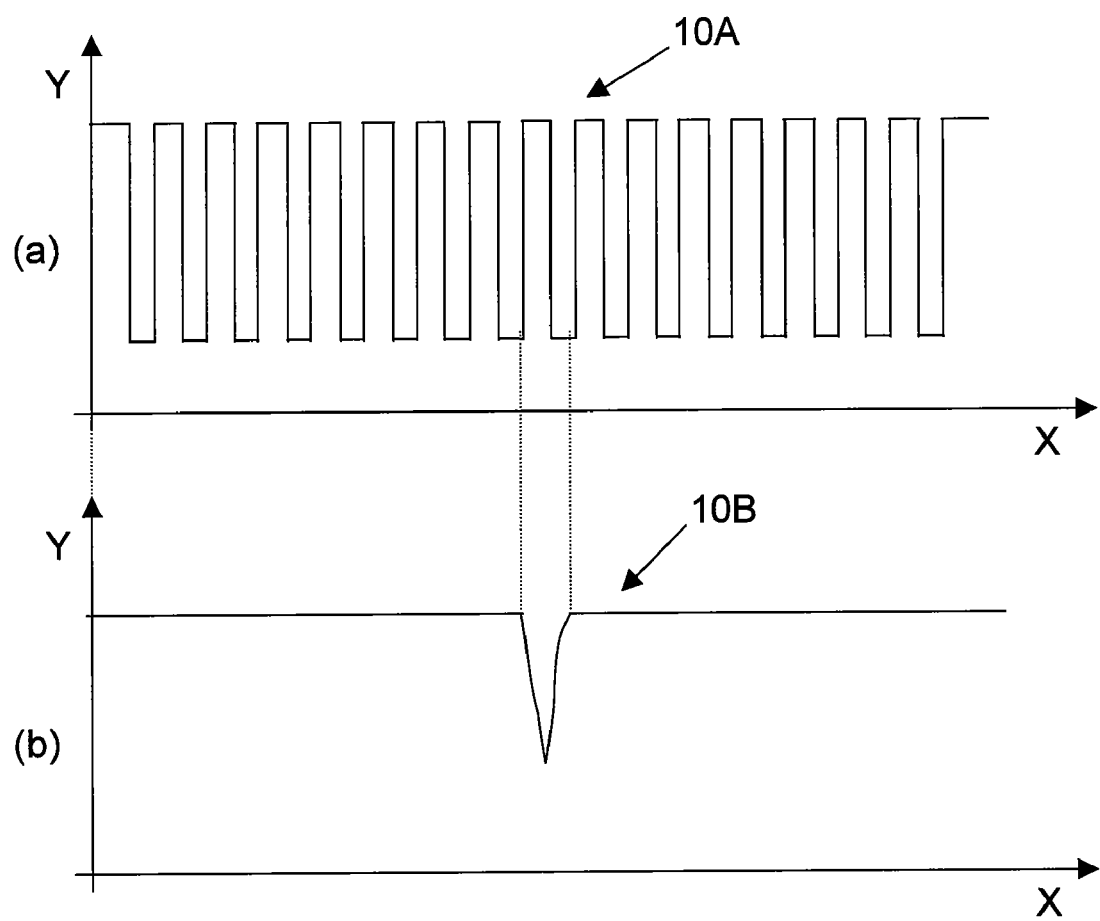
FIG. 10 illustrates graphs for typically showing the profiles obtained by processing the image shown in FIG. 9.

With regard to the two-dimensional data obtained by the first data processing procedure and subsequently recorded in the recording means 8, the places where lightness changes occur include a place near the vibrating yarn $Y_3$ and the place of a fluff defect 11 in FIG. 9, and if profiles concerning contrast in the running direction of yarns are obtained respectively for the ranges 20 and 21 of FIG. 9 corresponding to the places where the lightness changes obtained by the first data processing procedure and the third data processing procedure occur, the profile 10A shown in FIG. 10 (*a*) and the profile 10B shown in FIG. 10 (*b*) can be obtained. In FIG. 10 (*a*) and FIG. 10 (*b*), the horizontal axis X represents pixel positions in the running direction of yarns, and the vertical axis Y represents pixel values.

That is, in the case where a lightness change is caused by the vibration of a yarn, if a profile concerning contrast is obtained in the running direction of yarns at the place where the lightness change occurs, the lightness data of the yarn and the lightness data of the yarn clearance are obtained alternately on the recorded two-dimensional data. Therefore, as shown in FIG. 10 (a), the profile 10A in which lightness changes occur periodically for a long time period can be obtained. On the other hand, in the case where a lightness change is a defect such as fluff, the lightness change appears only at the place where it occurs, without subsequent periodic lightness changes, and the profile 10B as shown in FIG. 10 (b) can be obtained. Therefore, if whether or not periodic lightness changes subsequently occur is confirmed, it can be distinguished whether a lightness change obtained by the third data processing procedure is caused by a defect occurring on a yarn or by the vibration of the yarn.

The method for confirming the periodicity of lightness changes is not especially limited, if the method allows the automatic monitoring of two-dimensional time-series data including the occurrence of a lightness change obtained by the first data processing procedure and allows the confirmation of whether or not there are subsequent periodic lightness changes in the data. For example, in the profile 10A shown in FIG. 10 (a), many minus peaks occur. Therefore, applicable is an algorithm of acquiring the profile data concerning contrast in the running direction of the yarn concerned from the two-dimensional time-series data including a lightness change obtained by the first data processing procedure, counting the minus peaks in the profile data and determining periodicity when there are minus peaks more than a predetermined number of minus peaks.

Further, as another means, applicable is an algorithm of applying Fourier transform to the two-dimensional time-series data including the occurrence of a lightness change obtained by the first data processing procedure and the third data processing procedure, to perform frequency analysis and determining periodicity when there is a peak in a certain frequency band.

If the vibration of a yarn can be distinguished from a defect such as fluff according to the above-mentioned procedure, the conditions of the process can be finely monitored on the basis of types of occurring disorders. In the case where it is not required to identify the vibration of a yarn as a defect, the portion determined to be the vibration of a yarn can be exempted from inspection, to remove the effect of the vibration of any yarn, for allowing only the occurrences of defects such as fluff to be detected.

If an alarm device that can receive signals from the second data processing procedure and report the occurrences of defects is used, the occurrence of any defect can be known instantaneously. In this case, if a defect is the deposition of a fluff or fuzz on a running yarn, the defect can be removed in the production process. If a monitor for displaying the defect occurrence position obtained by the data processing procedure is installed in the yarn production site, or if multiple alarm devices are installed in parallel to each other in the transverse direction of yarns, to correspond to the defect occurrence positions to be obtained by the data processing procedure, which position in the transverse direction each defect occurs at or which yarn has the defect can be known instantaneously.

Whenever a defect occurs, the defect occurrence position and the yarn having the defect can be specified by data processing in the first data processing procedure. Therefore, if the defect data of every yarn is recorded with the lapse of time into the recording mean 8, the appearance quality of the yarns or the yarn packages obtained by winding the yarns can be determined for quality control, for example, by comparing the recorded defect data of the yarns with the yarn appearance quality criterion. With regard to the package obtained by winding each yarn with such inspection results, not only whether or not the package has defects but also the number and positions of the defects of the package can be known from the inspection results. Therefore, for example in a process for producing a textile product using the package, defective portions can be removed on the basis of the defect occurrence positions obtained as inspection results, or the inspection results can be used as quality assurance for the customer.

The method of the invention according to exemplary embodiments has been explained on the basis of the inspection data acquiring and processing equipment 1 comprising a set of the first illumination means 2a, the second illumination means 2b and the imaging means 3 shown in FIGS. 1 and 2. However, in the case where the number of yarns to be inspected is further larger than that can be inspected by this inspection data acquiring and processing equipment 1, an inspection data acquiring and processing equipment comprising at least two sets, each comprising the first illumination means, the second illumination means and the imaging means, can be used.

Figure 3:
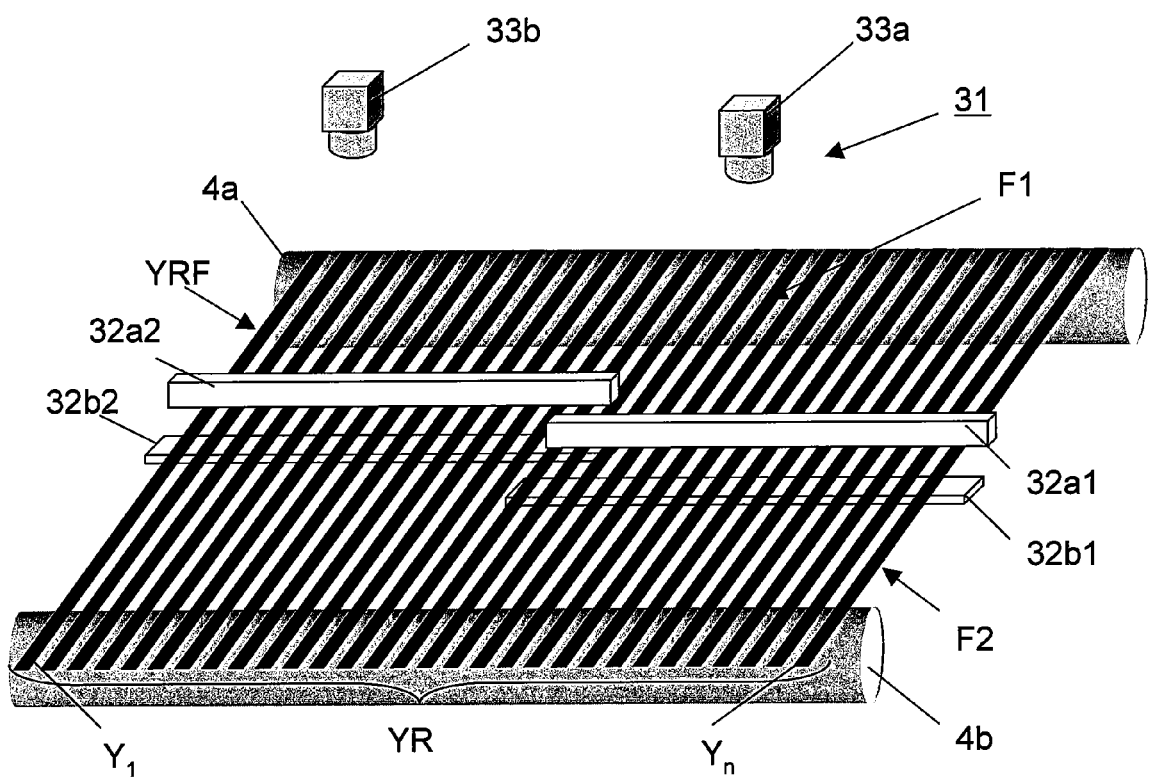
FIG. 3 is a schematic perspective view showing another example of inspection data acquiring and processing equipment for acquiring and processing the inspection data used for carrying out the running yarn inspection method in an embodiment of the invention.

FIG. 3 is a schematic perspective view showing another example of the inspection data acquiring and processing equipment for acquiring and processing the inspection data used for carrying out the running yarn inspection method of the invention in one embodiment. In FIG. 3, an inspection data acquiring and processing equipment 31 has two first illumination means 32a1 and 32a2, two second illumination means 32b1 and 32b2 and two imaging means 33a and 33b. The inspection data acquiring and processing equipment 31 of FIG. 3 also has the same data processing procedures as those shown as a block diagram in FIG. 1, but the procedures are not shown in FIG. 3. The inspection data acquiring and processing equipment 1 of FIG. 1 and the inspection data acquiring and processing equipment 31 of FIG. 3 are different only in the number of sets, each comprising a first illumination means, a second illumination means and an imaging means. Therefore, the inspection data acquiring and processing equipment 31 of FIG. 3 is not explained in detail here.

For carrying out the method of the invention in one embodiment, received light data and image data are processed, but since well-known conventional methods are used for processing these data, those methods are not explained in detail here either.

EXAMPLES

Example 1

The inspection data acquiring and processing equipment 1 used in this example comprises the followings.

First illumination means 2a: A fluorescent lamp turned on by a high frequency power source (40 W)

Distance $\alpha$ between first illumination means and yarns: 50 mm

Imaging means 3: Line sensor e-7450D (7450 pixels) produced by NED Company

Second illumination means 2b: Acrylic white plate (reflectance 30 to 80%)

Distance between second illumination means and yarns: 50 mm

Angle $\beta$ formed between the visual field of line sensor and yarns: 90°

Angle $\gamma$ formed between illumination light and yarns: 30°

Addition times of first data processing procedure: 5

Threshold value of second data processing procedure: 20

The above-mentioned constitution was used to inspect 50 yarns made to run in parallel to each other in a plane at a speed of 20 m/min at a place immediately before a yarn winding step, for detecting fluff defects. In the inspection, all of the first data processing procedure, the second data processing procedure and the third data processing procedure were used for data processing.

Concurrently with the above inspection, the same 50 yarns were visually inspected by two inspectors. Since the number of yarns to be inspected was 50, two inspectors were used.

As a result, all the fluff defects of the every yarn detected by the inspectors could be detected without any omission. It was confirmed that the inspection results obtained by the method of the invention in exemplary embodiments can be used for determining the appearance quality of the yarns and the yarn packages obtained by winding the yarns and are effective for quality control. Therefore, it could be confirmed that if the method of the invention is applied to a yarn production process, at least two inspectors can be reduced. It could also be confirmed that the defect data can be used to control a yarn production process in reference to the increase or decrease in the number of occurring defects, for enhancing the yield.

Whenever a lightness difference occurred in the third data processing procedure, profile data concerning contrast in the running direction of yarns at the position where the lightness difference occurred was obtained from the two-dimensional data obtained by the first data processing procedure. The number of minus peaks in the profile data was counted and when the number of minus peaks was 10 or more, the lightness difference was determined to be based on the vibration of a yarn for distinction from defect data such as fluff. The data distinguished like this was recorded into the recording means 8. Thus, the process could be improved timely in terms of both yarn vibration and yarn defects such as fluff.

According to the method of the invention in exemplary embodiments, numerous yarns running in parallel to each other can be simultaneously inspected online, to detect defects, for obtaining the information on the defects of every yarn. Therefore, the quality control of yarns and yarn packages can be appropriately performed. The method of the invention according to an exemplary embodiment can be suitably used for yarn manufacturing processes or yarn treatment and processing processes in which yarns can be produced while determining the existence or nonexistence of defects or the conditions of such defects of existing.

The invention claimed is:

1. A running yarn inspection method for inspecting multiple yarns running in parallel to each other in a plane comprising:
   (a) illuminating a yarn running plane from a first face side of the yarn running plane and a second face side of the yarn running plane and receiving light reflected from every yarn and light transmitted through clearances formed between respectively adjacent yarns simultaneously at a location faced to a first face of the yarn running plane by a sensor,
   (b) processing received light data obtained by the sensor, by a data processor, and
   (c) recording a part or all of the data obtained by the data processor, into a recorder with a lapse of time, wherein
   (d) data processing by the data processor comprises:
   (d-1) specifying positions of the yarns from the received light data and calculating yarn widths at the positions of the yarns and lightness values in a transverse direction of the yarns in a first data processing procedure, and
   (d-2) comparing data obtained by the first data processing procedure with a predetermined threshold value in a second data processing procedure, and/or calculating a difference between data obtained by adding and averaging data obtained by the first data processing procedure for a first predetermined number of scanning times and data obtained by adding and averaging data obtained by the first data processing procedure for a second predetermined number of scanning times consecutive to the first predetermined number of scanning times in a running direction of the yarns in a third data processing procedure.

2. The running yarn inspection method according to claim 1, wherein the sensor is a line sensor.

3. The running yarn inspection method according to claim 1, wherein data obtained from the second data processing procedure and/or the third data processing procedure is used to specify defects of yarns and/or yarns having defects.

4. The running yarn inspection method according to claim 1, wherein the illumination from the second face side is obtained by reflecting the illumination from the first face side by a reflection plate installed on the second face side.

5. The running yarn inspection method according to claim 1, wherein the sensor, a visual field of the sensor on the running yarn plane and the illumination from the second face side are positioned on one straight line, and the sensor is positioned at a location not receiving a regular reflection light of the illumination from the first face side on the running yarn plane.

6. The running yarn inspection method according to claim 1, wherein the difference obtained by the third data processing procedure from the lightness values in the transverse direction of the yarns at the positions specified by the first data processing procedure are compared with a threshold value predetermined by the second data processing procedure.

7. The running yarn inspection method according to claim 1, wherein only data portions including yarns having defects are extracted from temporally continuous lightness data obtained by the first data processing procedure and are stored as two-dimensional data by the recorder.

8. The running yarn inspection method according to claim 1, wherein whether or not lightness difference data obtained by the data processor is periodic is determined.

9. A carbon fiber production process comprising treating multiple precursor yarns each of which comprises a bundle of numerous continuous filaments running parallel to each other for carbonization, letting multiple carbon fiber yarns run in parallel to each other in a plane, and winding the respective carbon fiber yarns, wherein the multiple carbon fiber yarns are inspected using the running yarn inspection method as set forth in claim 1 at a place where the multiple carbon fiber yarns run in parallel to each other in the plane.

* * * * *